(12) United States Patent
Thirring et al.

(10) Patent No.: US 9,061,980 B2
(45) Date of Patent: Jun. 23, 2015

(54) ORGANIC COMPOUNDS

(75) Inventors: Klaus Thirring, Vienna (AT); Werner Heilmayer, Zillingtal (AT)

(73) Assignee: NABRIVA THERAPEUTICS, AG, Vienna (AT)

( * ) Notice: Subject to any disclaimer, the term of this patent is extended or adjusted under 35 U.S.C. 154(b) by 734 days.

(21) Appl. No.: 12/668,690

(22) PCT Filed: Jul. 11, 2008

(86) PCT No.: PCT/AT2008/000255
§ 371 (c)(1),
(2), (4) Date: Jan. 29, 2010

(87) PCT Pub. No.: WO2009/009813
PCT Pub. Date: Jan. 22, 2009

(65) Prior Publication Data
US 2010/0190855 A1    Jul. 29, 2010

(30) Foreign Application Priority Data
Jul. 13, 2007    (EP) .................................... 07450123

(51) Int. Cl.
| | | |
|---|---|---|
| C07C 69/712 | (2006.01) | |
| C07C 323/52 | (2006.01) | |
| C07C 71/00 | (2006.01) | |
| A61K 31/216 | (2006.01) | |

(52) U.S. Cl.
CPC .............. *C07C 323/52* (2013.01); *A61K 31/216* (2013.01); *C07C 69/712* (2013.01); *C07C 2101/14* (2013.01); *C07C 2103/99* (2013.01)

(58) Field of Classification Search
CPC .. A61K 31/216; C07C 69/712; C07C 323/52; C07C 2101/14; C07C 2103/99
USPC ............................................. 514/532; 560/61
See application file for complete search history.

(56) References Cited

U.S. PATENT DOCUMENTS 3,979,423 A * 9/1976 Riedl .............................. 558/52
2007/0167495 A1* 7/2007 Brown et al. ................. 514/345

FOREIGN PATENT DOCUMENTS

| GB | 1 312 148 | 4/1973 |
|---|---|---|
| WO | 01/09095 A1 | 2/2001 |
| WO | WO 0174788 A1 * | 10/2001 |
| WO | 2007/079515 A1 | 7/2007 |
| WO | WO 2007079515 A1 * | 7/2007 |

OTHER PUBLICATIONS http://medical-dictionary.thefreedictionary.com/pharmaceutical.*
Dykhuizen, Antonie van Leeuwenhoek, 1998, Kluwer Academic Publishers, vol. 73, pp. 25-33.*
Chen et. al., Journal of Medicinal Chemistry, 2001, American Chemical Society, vol. 44, pp. 2374-2377.*
Foroumadi et. al., European Journal of Medicinal Chemistry, 2003, Elsevier, vol. 38, pp. 851-854.*
CLSI, former National Committee for Clinical Laboratory Standards (NCCLS) 2006, Document M7-A7 vol. 26, No. 2: Methods for dilution Antimicrobial Susceptibility Tests for Bacteria that Grow Aerobically—Seventh Edition, Approved Standard.
National Committee for Clinical Laboratory Standards (NCCLS) vol. 24, No. 2, M11-A6, Methods for Antimicrobal Susceptibility Testing of Anaerobic Bacteria; Approved Standard; Sixth Edition (2004).
The Merck Index, 12th edition, item 7694.

* cited by examiner

*Primary Examiner* — Sarah Pihonak
(74) *Attorney, Agent, or Firm* — Workman Nydegger

(57) ABSTRACT

A compound of formula (I) wherein Y is oxygen or sulfur, and $X_1$, $X_2$ and $X_3$ are independently of each other hydrogen, halogen, hydroxy or linear or branched $(C_{1-6})$-alkoxy, or hydroxy-$(C_{1-6})$alkyl or $(C_{1-6})$alkoxy-$(C_{1-6})$alkyl, mono- or dihalogenated $(C_{1-6})$-alkyl, amino$(C_{1-6})$-alkyl, hydroxy $(C_{1-6})$-alkyl, with one of the two provisos that: (1) at least of $X_1$, $X_2$ and $X_3$ is other than hydrogen, and (2) $X_2$ is other than hydroxy, when $X_1$ and $X_3$ are hydrogen.

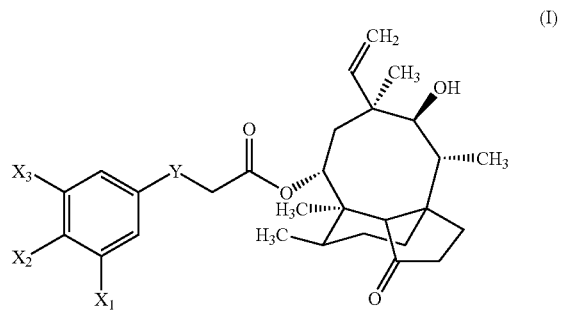

20 Claims, No Drawings

ORGANIC COMPOUNDS

The present invention relates to organic compounds, such as pleuromutilins.

Pleuromutilin, a compound of formula

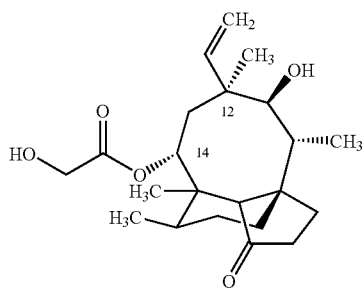

is a naturally occurring antibiotic, e.g. produced by the basidomycetes *Pleurotus mutilus* and *P. passeckerianus*, see e.g. The Merck Index, 12th edition, item 7694. A number of further pleuromutilins containing the ring structure principle of pleuromutilin and being substituted at the hydroxy group have been developed, e.g. as antimicrobials.

We have now found pleuromutilins with interesting activity.

In one aspect the present invention provides a pleuromutilin of formula (I)

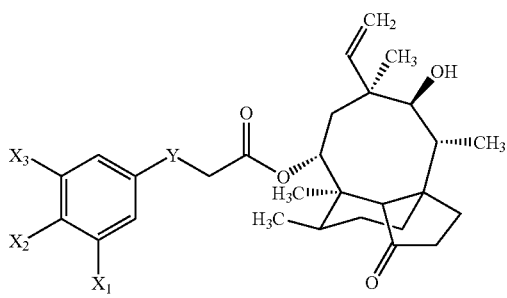

wherein
Y is oxygen or sulfur, and
$X_1$, $X_2$ and $X_3$ are independently of each other hydrogen, halogen, hydroxy or linear or branched $(C_{1-6})$alkoxy, or hydroxy-$(C_{1-6})$alkyl or $(C_{1-6})$alkoxy-$(C_{1-6})$alkyl, mono- or dihalogenated $(C_{1-6})$-alkyl, amino$(C_{1-6})$-alkyl, hydroxy$(C_{1-6})$-alkyl, with one of the two provisos, e.g. with both provisos, that
(1) at least one of $X_1$, $X_2$ and $X_3$ is other than hydrogen, and
(2) $X_2$ is other than hydroxy, when $X_1$ and $X_3$ are hydrogen.

In one aspect $X_1$, $X_2$ and $X_3$ are independently of each other are hydrogen or halogen;

In another aspect $X_1$, $X_2$ and $X_3$ are independently of each other are hydrogen or hydroxy;

In another aspect $X_1$, $X_2$ and $X_3$ are independently of each other are hydrogen or $(C_{1-6})$alkoxy;
with one of the two provisos, e.g. with both provisos, as indicated above.

Halogen as defined herein includes fluoro, chloro, bromo and iodo, preferably fluoro. Alkoxy as defined herein includes $(C_{1-6})$alkoxy, such as $(C_{1-4})$alkoxy, e.g. methoxy.

Preferred compounds according to the invention are selected from the group consisting of
14-O-[(3-Fluoro-phenylsulfanyl)-acetyl]-mutilin,
14-O-[(4-Fluoro-phenylsulfanyl)-acetyl]-mutilin,
14-O-[(3,5-Difluoro-phenylsulfanyl)-acetyl]-mutilin,
14-O-[(3,4-Difluoro-phenylsulfanyl)-acetyl]-mutilin,
14-O-[(3-Hydroxy-phenylsulfanyl)-acetyl]-mutilin,
14-O-[(3-Methoxy-phenylsulfanyl)-acetyl]-mutilin,
14-O-[(4-Methoxy-phenylsulfanyl)-acetyl]mutilin,
14-O-[(3,4-Dimethoxy-phenylsulfanyl)-acetyl]mutilin,
14-O-[(3-Hydroxy-phenoxy)-acetyl]-mutilin,
14-O-[(4-Hydroxy-phenoxy)-acetyl]-mutilin,
14-O-[(3,5-Dihydroxy-phenoxy)-acetyl]-mutilin.

It turned out that the antimicrobial activity against clinical relevant bacterial pathogens (*Staphylococcus aureus*, *Enterococcus faecalis*, *Streptococcus pneumoniae*, *Moraxella catarrhalis* and *Escherichia coli*, see Table 1 hereinafter) of said pleuromutilin-derivatives is particularly enhanced when the phenyl-ring carries substituents $X_1$, $X_2$ and $X_3$ mentioned above in meta and/or para position in relation to the oxygen/sulfur bound to the phenyl-ring.

A compound provided by the present invention is herein also designated as "compound(s) of (according to) the present invention". A compound of the present invention includes mutilin-14-yl acetic acid esters, e.g. as explicitly defined above, and a compound of formula I. A compound of the present invention includes a compound in any form, e.g. in free form, in the form of a salt, in the form of a solvate and in the form of a salt and a solvate.

The compounds of the present invention may be in crystalline or non-crystalline form, and, if crystalline, may optionally be hydrated or a solvate. When some of the compounds of this invention are allowed to crystallise or are recrystallised from organic solvents, solvent of crystallisation may be present in the crystalline product.

This invention includes within its scope such solvates. Similarly, some of the compounds of this invention may be crystallised or recrystallised from solvents containing water. In such cases water of hydration may be present in the crystalline product. This invention includes within its scope stoichiometric hydrates as well as compounds containing variable amounts of water that may be produced by processes such as lyophilisation.

In another aspect the present invention provides a compound of the present invention in the form of a salt.

Such salts include preferably pharmaceutically acceptable salts, although pharmaceutically unacceptable salts are included, e.g. for preparation/isolation/purification purposes.

A salt of a compound of the present invention includes a metal salt or an acid addition salt. Metal salts include for example alkali or earth alkali salts; acid addition salts include salts of a compound of the present invention with an acid, e.g. hydrogen fumaric acid, fumaric acid, naphthalin-1,5-sulphonic acid, hydrochloric acid, deuterochloric acid; preferably hydrochloric acid.

A compound of the present invention in free form may be converted into a corresponding compound in the form of a salt; and vice versa. A compound of the present invention in free form or in the form of a salt and in the form of a solvate may be converted into a corresponding compound in free form or in the form of a salt in non-solvated form; and vice versa.

A compound of the present invention, if substituted accordingly, may exist in the form of isomers and mixtures thereof; e.g. optical isomers, diastereoisomers, cis/trans conformers. A compound of the present invention may e.g. contain asymmetric carbon atoms and may thus exist in the form of enantiomers or diastereoisomers and mixtures thereof, e.g. racemates. Substituents at any asymmetric carbon atom may be present in the (R)-, (S)- or (R,S)-configuration, preferably in the (R)- or (S)-configuration. E.g., if in a compound of formula I $R_1$ is substituted alkyl and that substituent is attached to a carbon atom of the side chain of such alkyl, the carbon atom to which such substituent is attached is an asymmetric carbon atom and such substiutent may be in the (R)- and (S)-configuration, including mixtures thereof. The configuration of substituents attached to asymmetric carbon atoms of the mutilin-ring is preferably the same as in natural pleuromutilin.

Isomeric mixtures may be separated as appropriate, e.g. according, e.g. analogously, to a method as conventional, to obtain pure isomers. The present invention includes a compound of the present invention in any isomeric form and in any isomeric mixture. The present invention also includes tautomers of a compound of the present invention, where tautomers can exist.

Any compound described herein, e.g. a compound of the present invention and intermediates in their production may be prepared as appropriate, e.g. according, e.g. analogously, to a method as conventional, e.g. or as specified herein.

A compound may be converted into a corresponding salt, according, e.g. analogously, to a method as conventional, e.g. by treatment with an acid, or, metal base, respectively, to obtain an acid addition salt, or, a metal salt, respectively and vice versa, a compound obtained by a process provided by the present invention in the form of a salt, may be converted into the corresponding compound in the form of a free base, according, e.g. analogously, to a method as conventional, e.g. by treatment with an acid if a metal salt is obtained and by treating with a metal base, e.g. a metal hydroxide if an acid addition salt is obtained.

For example, the compounds of the present invention show antimicrobial, e.g. antibacterial, activity against gram positive bacteria, such as coagulase-positive and coagulase-negative *Staphylococci*, e.g. *Staphylococcus aureus, Styphylococcus epidermis, Staphylococcus haemolyticus, Streptococci*, e.g. *Streptococcus pyogenes, Streptococcus pneumoniae, Streptococcus agalacticae, Enterococci*, e.g. *Enterococcus faecium* and *Moraxellaceae*, e.g. *Moraxella catarrhalis*, Pasteurellaceae, e.g. *Haemophilus influenzae*, as well as against Mycoplasmactaceae, *Chlamydiaceae*, e.g. *Chlamydia trachomatis, Chlamydia pneumoniae* and obligatory anaerobes, e.g. *Bacteroides fragilis, Clostridium difficile*; in vitro in the Agar Dilution Test or Microdilution Test according to the Clinical and Laboratory Standards Institute (CLSI, former National Committee for Clinical Laboratory Standards (NCCLS) 2006, Document M7-A7 Vol. 26, No. 2: "Methods for dilution Antimicrobial Susceptibility Tests for Bacteria that Grow Aerobically—Seventh Edition, Approved Standard"; and in the in vitro determination of the antibacterial activity against anaerobic bacteria according to National Committee for Clinical Laboratory Standards (NCCLS) VOL. 24, No. 2, M11-A5, Methods for Antimicrobal Susceptibility Testing of Anaerobic Bacteria; Approved Standard; Sixth Edition (2004) and in vivo in the septicaemic mouse model against *Staphylococcus aureus*.

Compounds of the present invention are therefore suitable for the treatment and prevention of diseases which are mediated by microbes, e.g. by bacteria. Diseases which also may be treated include e.g. diseases mediated by *Helicobacter*, such as *Helicobacter pylori*, and diseases mediated by *Mycobacterium tuberculosis*, diseases mediated by *Legionella pneumophila* or Neisseriaceae, diseases which also may be treated include in general inflammatory diseases, where microbes are mediating said inflammation, e.g. including acne.

Compounds of the present invention are preferably useful to treat skin and soft tissue infections, for example epidermal infections like impetigo, bullous impetigo or eethyma, dermal infections like erysipelas, cellulites, erythrasma or necrotizing fasciitis, follicular infections like folliculitis, furunculosis or carbunculosis, other infections like paronychia, dactylitis, botryomycosis, mastitis, secondarily infected skin lesions, secondarily infected dermatoses, for the decolonization of bacterial carriers, e.g. decolonization of nasal *Staphylococcus aureus* carriers, and acne, by topical application. Accordingly, in a further aspect the present invention provides the use of a compound of the invention or a pharmaceutically acceptable salt or derivative or solvate thereof in the preparation of a medicament adapted for topical administration for use in the treatment of skin and soft tissue infections and also in the treatment of acne in humans. The invention also provides the use of a compound of the invention, or a pharmaceutical acceptable derivative thereof, in the manufacture of a medicament for use in the treatment of a skin or soft tissue infection.

In another aspect the present invention provides a compound of the present invention for use as a pharmaceutical, preferably as an antimicrobial, such as an antibiotic, e.g. and an anti-anaerobic.

In another aspect the present invention provides a compound of the present invention for use in acne treatment.

In a further aspect the present invention provides a compound of the present invention for use in the preparation of a medicament for the treatment of diseases, mediated by microbes, such as bacterials, for example diseases mediated by bacteria, e.g. selected from *Staphylococci, Streptococci, Enterococci*;
diseases mediated by *Helicobacter*
diseases mediated by *Legionella*, Neisseriaceae, *Moraxellaceae, Pasteurellaceae, Corynebacteria*,
diseases mediated by *Mycobacterium tuberculosis*,
e.g. diseases mediated by Mycoplasmataceae, *Chlamydiaceae* and obligatory anaerobes,
for the treatment of acne, and/or
for the decolonization of individuals colonized with bacteria.

In a further aspect the present invention provides a method of treatment of diseases mediated by microbes which comprises administering to a subject in need of such treatment an effective amount of a compound of the present invention e.g. in the form of a pharmaceutical composition.

In a further aspect the present invention provides a method of treatment of acne which comprises administering to a subject in need of such treatment an effective amount of a compound of the present invention e.g. in the form of a pharmaceutical composition.

Treatment includes treatment and prophylaxis.

For antimicrobial and acne treatment, the appropriate dosage will, of course, vary depending upon, for example, the chemical nature and the pharmakokinetic data of a compound of the present invention employed, the individual host, the mode of administration and the nature and severity of the conditions being treated. However, in general, for satisfactory results in larger mammals, for example humans, an indicated daily dosage is in the range from about 0.01 to 3 g of a compound of the present invention conveniently administered, for example, in divided doses up to four times a day.

A compound of the present invention may be administered by any conventional route, for example enterally, e.g. including nasal, buccal, rectal, oral, administration; parenterally, e.g. including intravenous, intramuscular, subcutanous administration; or topically, e.g. including epicutaneous, intranasal, intratracheal administration, e.g. in form of coated or uncoated tablets, capsules, injectable solutions or suspensions, e.g. in the form of ampoules, vials, in the form of semi-solid formulations, e.g. ointments, creams, gels, pastes, in the form of inhaler powder, foams, tinctures, lip sticks, concealer sticks, drops, sprays, or in the form of suppositories, e.g. in analogous manner to macrolides, such as erythromycins, e.g. clarithromycin or azithromycin.

A compound of the present invention may be administered in the form of a pharmaceutically acceptable salt, e.g. an acid addition salt or metal salt; or in free form; optionally in the form of a solvate. A compound of the present invention in the form of a salt exhibit the same order of activity as the compound in free form; optionally in the form of a solvate.

A compound of the present invention may be used for pharmaceutical treatment according to the present invention alone or in combination with one or more other pharmaceutically active agents. Such other pharmaceutically active agents include e.g. other antibiotics and antiinflammatory agents, and, if a compound of the present invention is used in the treatment of acne, other pharmaceutically agents include furthermore agents which are active against acne or used for the decolonization/sterilisation of bacterial carriers. Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising a compound of the present invention, e.g. including a compound of formula I, in free form or in the form of a pharmaceutically acceptable salt; e.g. and/or in the form of a solvate; in association with at least one pharmaceutical, excipient, e.g. carrier or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

In another aspect the present invention provides a pharmaceutical composition according to the present invention, further comprising another pharmaceutically active agent.

Such pharmaceutical compositions may be manufactured according, e.g. analogously, to a method as conventional, e.g. by mixing, granulating, coating, dissolving or lyophilizing processes.

Unit dosage form may contain, for example, from about 0.01 mg to about 3000 mg, such as 1 mg to about 1000 mg.

The compounds of the present invention are additionally suitable as veterinary agents, e.g. veterinary active compounds, e.g. in the prophylaxis and in the treatment of microbial, e.g. bacterial diseases, in animals, such as fowl, pigs and calves; e.g. and for diluting fluids for artificial insemination and for egg-dipping techniques.

In another aspect the present invention provides a compound of the present invention for use as a veterinary agent.

In a further aspect the present invention provides a compound of the present invention for the preparation of a veterinary composition which is useful as a veterinary agent.

In another aspect the present invention provides a veterinary method for the prophylaxis and in the treatment of microbial, e.g. bacterial diseases which comprises administering to a subject in need of such treatment an effective amount of a compound of the present invention, e.g. in the form of a veterinary composition.

For use of the active compounds of the present invention as a veterinary agent, the dosage will of course vary depending upon the size and age of the animal and the effect desired; for example for prophylactic treatment relatively low doses would be administered over a longer time period, e.g. 1 to 4 weeks. Preferred doses in drinking water are from 0.0125 to 0.05 weight by volume, particularly 0.0125 to 0.025; and in foodstuffs from 20 to 400 g/metric ton, preferably 20 to 200 g/metric ton. It is preferred to administer the active compounds of the present invention as a veterinary agent to hens in drinking water, to pigs in foodstuff and to calves orally or parenterally, e.g. in the form of oral or parenteral preparations.

The invention is further described by reference to the following examples. These examples are provided for illustration purposes only and are not intended to be limiting the present invention in any way.

EXAMPLES

Example 1

14-O-[(3-Fluoro-phenylsulfanyl)-acetyl]-mutilin

Step 1: Pleuromutilintosylate

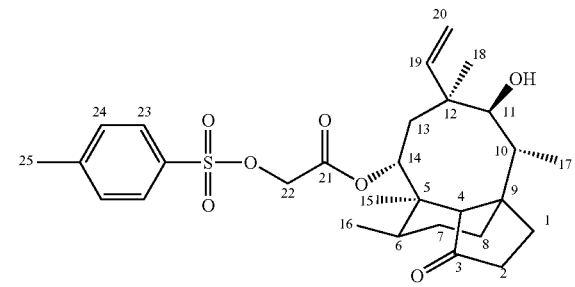

To a solution of 18.63 g (49.2 mmol) of Pleuromutilin and 9.39 g (49.2 mmol) of toluenesulfonylchloride in 1400 mL of methylethylketone a solution of 4.98 g (49.2 mmol) of triethylamine in 300 mL of methylethylketone is slowly added at ambient temperature. The reaction is stirred for 24 h at ambient temperature, the formed precipitate is filtered off and 2800 mL of water is added to the solution. The solution is extracted three times with ethyl acetate, the organic phase is dried with $Na_2SO_4$ and evaporated to dryness under reduced pressure. The crude product is used for the next step without further purification.

$^1$H-NMR (400 MHz, DMSO-$d_6$, δ, ppm, characteristic signals): 0.49 (d, 3H, J=7Hz, $CH_3$-16); 0.8 (d, 3H, J=7Hz, $CH_3$-17); 1.02 (s, 3H, $CH_3$-18); 1.29 (s, 3H, $CH_3$-15); 2.38 (bs, 1H, H-4); AB-system ($U_A$=4.75, $U_B$=4.62, J=16Hz, $CH_2$-22); 5.00 (m, 2H, H-20); 5.52 (d, 1H, J=8Hz, H-14); 6.04 (dd, 1H, J=11 and 18Hz, H-19); 7.46 (d, 2H, J=8Hz, H-24); 7.79 (d, 2H, J=8Hz, H-23).

Step 2: 14-O-[(3-Fluoro-phenylsulfanyl)-acetyl]-mutilin

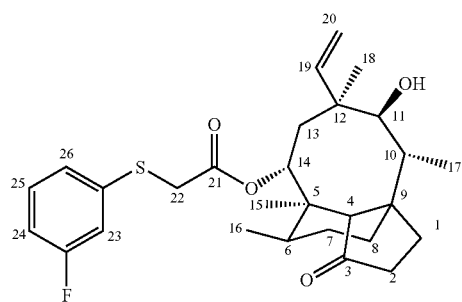 [SMILES: C=C[C@]1(C)C[C@@H](OC(=O)CSc2cccc(F)c2)[C@]2(C)C(C)CCC3(CCC(=O)C32)[C@@H](C)[C@@H]1O]

To 1 g (7.8 mmol) of 3-Fluoro-benzenethiol in 30 mL of absolute ethanol 530 mg (7.8 mmol) of sodium ethoxide is added. After stirring the reaction for 30 min at ambient temperature a solution of 4.15 g (7.8 mmol) of Pleuromutilintosylate in 30 mL of acetone is added and the reaction stirred at ambient temperature for 2h. The reaction mixture is evaporated to dryness under reduced pressure, dissolved in ethyl acetate and extracted three times with water. The organic phase is dried with $Na_2SO_4$, evaporated to dryness under reduced pressure and the residue is chromatographed on silica gel using dichloromethane ⟶ dichloromethane/methanol 100:1.2 as mobile phase.

$^1$H-NMR (500 MHz, $CDCl_3$, δ, ppm, characteristic signals): 0.70 (d, 3H, J=7Hz, $CH_3$-16); 0.88 (d, 3H, J=7Hz, $CH_3$-17); 1.13 (s, 3H, $CH_3$-18); 1.44 (s, 3H, $CH_3$-15); 2.09 (bs, 1H, H-4); 3.35 (t, 1H, J=6Hz, H-11); 3.60 (s, 2H, $CH_2$-22); 5.17 and 5.32 (2xdd, 2H, $J_1$=1 and 17Hz, $J_2$=1 and 11Hz, H-20); 5.76 (d, 1H, J=8 Hz, H-14); 6.41 (dd, 1H, J=11 and 17Hz, H-19); 6.91 (m, 1H, H-24); 7.08 and 7.14 (2xm, 2H, H-23 and 26); 7.26 (m, 1H, H-25).

The following compounds are prepared in a similar fashion:

Example 2

14-O-[(4-Fluoro-phenylsulfanyl)-acetyl]mutilin

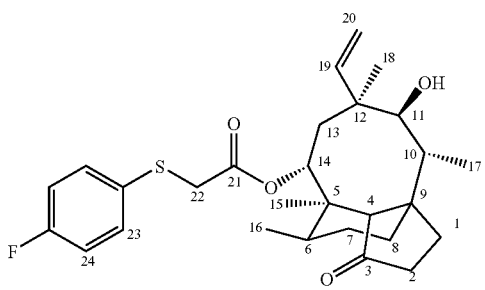 [SMILES: C=C[C@]1(C)C[C@@H](OC(=O)CSc2ccc(F)cc2)[C@]2(C)C(C)CCC3(CCC(=O)C32)[C@@H](C)[C@@H]1O]

$^1$H-NMR (400 MHz, DMSO-$d_6$, δ, ppm, characteristic signals): 0.53 (d, 3H, J=7Hz, $CH_3$-16); 0.78 (d, 3H, J=7Hz, $CH_3$-17); 0.98 (s, 3H, $CH_3$-18); 1.28 (s, 3H, $CH_3$-15); 2.35 (bs, 1H, H-4); 3.37 (t, 1H, J=6Hz, H-11); AB-system ($U_A$=3.80, $U_B$=3.73, J=15Hz, $CH_2$-22); 4.93 (m, 2H, H-20); 5.48 (d, 1H, J=8Hz, H-14); 6.02 (m, 1H, H-19); 7.12 (m, 2H, H-23); 7.42 (m, 2H, H-24).

Example 3

(Comparison):
14-O-[(2-Fluoro-phenylsulfanyl)-acetyl]-mutilin

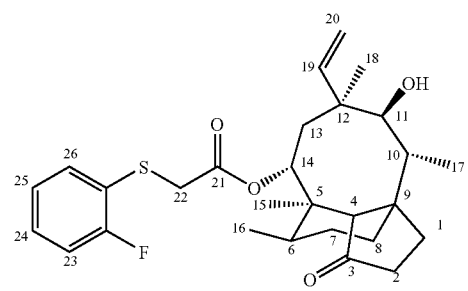 [SMILES: C=C[C@]1(C)C[C@@H](OC(=O)CSc2ccccc2F)[C@]2(C)C(C)CCC3(CCC(=O)C32)[C@@H](C)[C@@H]1O]

$^1$H-NMR (400 MHz, DMSO-$d_6$, δ, ppm, characteristic signals): 0.53 (d, 3H, J=7Hz, $CH_3$-16); 0.78 (d, 3H, J=7Hz, $CH_3$-17); 0.98 (s, 3H, $CH_3$-18); 1.27 (s, 3H, $CH_3$-15); 2.37 (bs, 1H, H-4); 3.37 (t, 1H, J=6Hz, H-11); AB-system ($U_A$=3.85, $U_B$=3.78, J=16Hz, $CH_2$-22); 4.93 (m, 2H, H-20); 5.47 (d, 1H, J=8Hz, H-14); 6.02 (m, 1H, H-19); 7.19 and 7.42 (2xm, 4H, H-23, 24, 25 and 26).

Example 4

14-O-[(3,5-Difluoro-phenylsulfanyl)-acetyl]-mutilin

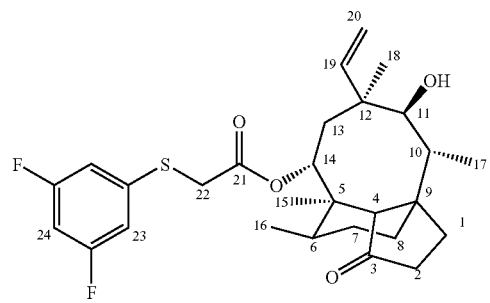 [SMILES: C=C[C@]1(C)C[C@@H](OC(=O)CSc2cc(F)cc(F)c2)[C@]2(C)C(C)CCC3(CCC(=O)C32)[C@@H](C)[C@@H]1O]

$^1$H-NMR (400 MHz, DMSO-$d_6$, δ, ppm, characteristic signals): 0.57 (d, 3H, J=7Hz, $CH_3$-16); 0.79 (d, 3H, J=7Hz, $CH_3$-17); 0.98 (s, 3H, $CH_3$-18); 1.30 (s, 3H, $CH_3$-15); 2.37 (bs, 1H, H-4); 3.38 (t, 1H, J=6Hz, H-11); AB-system ($U_A$=4.00, $U_B$=3.94, J=16Hz, $CH_2$-22); 4.92 (m, 2H, H-20); 5.50 (d, 1H, J=8Hz, H-14); 6.02 (m, 1H, H-19); 6.98-7.12 (m, 3H, H-23 and 24).

Example 5

14-O-[(3,4-Difluoro-phenylsulfanyl)-acetyl]-mutilin

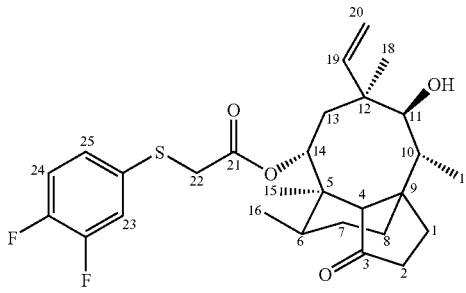

¹H-NMR (400 MHz, CDCl₃, δ, ppm, characteristic signals): 0.67 (d, 3H, J=7Hz, CH₃-16); 0.87 (d, 3H, J=7Hz, CH₃-17); 1.13 (s, 3H, CH₃-18); 1.41 (s, 3H, CH₃-15); 2.07 (bs, 1H, H-4); 3.33 (dd, 1H, J=7 and 11Hz, H-11); 3.52 (s, 2H, CH₂-22); 5.17 and 5.31 (2xdd, 2H, J₁=1 and 17Hz, J₂=1 and 11Hz, H-20); 5.74 (d, 1H, J=8Hz, H-14); 6.40 (dd, 1H, J=11 and 17Hz, H-19); 7.08, 7.13 and 7.23 (3×m, 3H, H-23, 24 and 25).

Example 6

(Comparison): 14-O-[(2,4-Difluoro-phenylsulfanyl)-acetyl]-mutilin

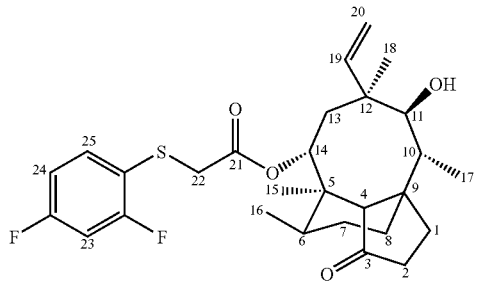 [SMILES: C=C[C@]1(C)C[C@@H](OC(=O)CSc2ccc(F)cc2F)[C@]2(C)C(C)CCC3(CCC(=O)C32)[C@@H](C)[C@@H]1O]

¹H-NMR (400 MHz, DMSO-d₆, δ, ppm, characteristic signals): 0.51 (d, 3H, J=7Hz, CH₃-16); 0.78 (d, 3H, J=7Hz, CH₃-17); 0.98 (s, 3H, CH₃-18); 1.26 (s, 3H, CH₃-15); 2.34 (bs, 1H, H-4); 3.37 (t, 1H, J=6Hz, H-11); AB-system (U_A=3.80, U_B=3.72, J=15Hz, CH₂-22); 4.93 (m, 2H, H-20); 5.45 (d, 1H, J=8Hz, H-14); 6.00 (m, 1H, H-19); 7.05 (m, 1H, H-24); 7.30 (m, 1H, H-23); 7.54 (m, 1H, H-25).

Example 7

14-O-[(3-Hydroxy-phenylsulfanyl)-acetyl]-mutilin

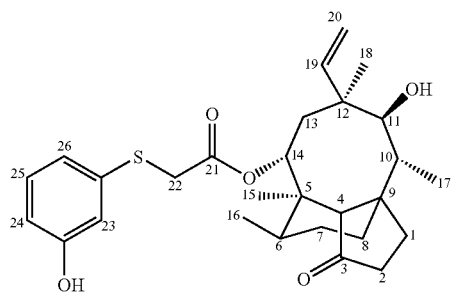 [SMILES: C=C[C@]1(C)C[C@@H](OC(=O)CSc2cccc(O)c2)[C@]2(C)C(C)CCC3(CCC(=O)C32)[C@@H](C)[C@@H]1O]

¹H-NMR (400 MHz, CDCl₃+CD₃OD, δ, ppm, characteristic signals): 0.68 (d, 3H, J=7Hz, CH₃-16); 0.87 (d, 3H, J=7Hz, CH₃-17); 1.11 (s, 3H, CH₃-18); 1.41 (s, 3H, CH₃-15); 2.07 (bs, 1H, H-4); 3.32 (d, 1H, J=7Hz, H-11); 3.56 (s, 2H, CH₂-22); 5.14 and 5.29 (2xdd, 2H, J₁=1 and 17 Hz, J₂=1 and 11Hz, H-20); 5.70 (d, 1H, J=8Hz, H-14); 6.37 (dd, 1H, J=11 and 17Hz, H-19); 6.66 and 6.84 (2xm, 2H, H-24 and 26); 6.83 (s, 1H, H-23); 7.10 (t, 1H, J=8Hz, H-25).

Example 9

(Comparison): 14-O-[(2-Hydroxy-phenylsulfanyl)-acetyl]-mutilin

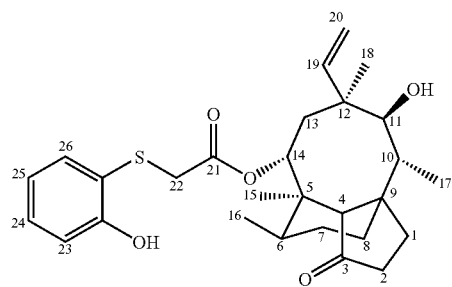 [SMILES: C=C[C@]1(C)C[C@@H](OC(=O)CSc2ccccc2O)[C@]2(C)C(C)CCC3(CCC(=O)C32)[C@@H](C)[C@@H]1O]

¹H-NMR (400 MHz, DMSO-d₆, δ, ppm, characteristic signals): 0.55 (d, 3H, J=7Hz, CH₃-16); 0.79 (d, 3H, J=7Hz, CH₃-17); 0.99 (s, 3H, CH₃-18); 1.29 (s, 3H, CH₃-15); 2.34 (bs, 1H, H-4); 3.39 (t, 1H, J=6Hz, H-11); AB-system (U_A=3.71, U_B=3.60, J=15Hz, CH₂-22); 4.94 (m, 2H, H-20); 5.47 (d, 1H, J=8Hz, H-14); 6.02 (dd, 1H, J=11, and 18Hz, H-19); 6.71 (t, 1H, J=8Hz, H-25); 6.79 (d, 1H, J=8Hz, H-23); 7.03 (t, 1H, J=8Hz, H-24); 7.16 (d, 1H, J=8Hz, H-26).

Example 10

14-O-[(3-Methoxy-phenylsulfanyl)-acetyl]-mutilin

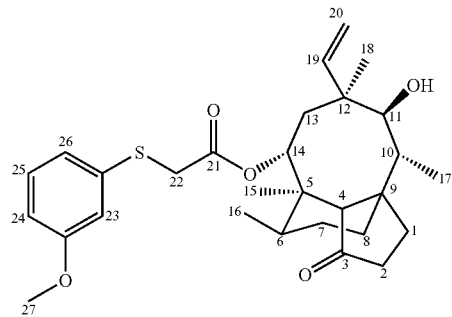 [SMILES: C=C[C@]1(C)C[C@@H](OC(=O)CSc2cccc(OC)c2)[C@]2(C)C(C)CCC3(CCC(=O)C32)[C@@H](C)[C@@H]1O]

¹H-NMR (400 MHz, DMSO-d₆, δ, ppm, characteristic signals): 0.56 (d, 3H, J=7Hz, CH₃-16); 0.79 (d, 3H, J=7Hz, CH₃-17); 0.97 (s, 3H, CH₃-18); 1.30 (s, 3H, CH₃-15); 2.35 (bs, 1H, H-4); 3.37 (t, 1H, J=6Hz, H-11); 3.72 (s, 3H, CH₃-27); AB-system (U_A=3.84, U_B=3.77, J=16Hz, CH₂-22); 4.93 (m, 2H, H-20); 5.49 (d, 1H, J=8Hz, H-14); 6.02 (m, 1H, H-19); 6.71 and 6.88 (2xm, 2H, H-24 and 26); 6.90 (s, 1H, H-23); 7.18 (t, 1H, J=8Hz, H-25).

Example 11

14-O-[(4-Methoxy-phenylsulfanyl)-acetyl]-mutilin

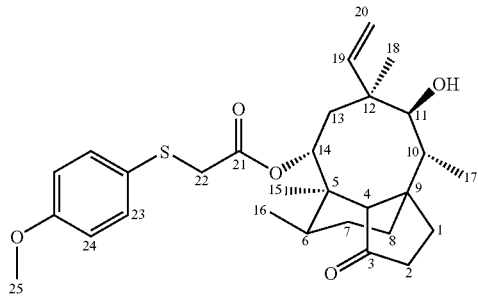 [SMILES: C=C[C@]1(C)C[C@@H](OC(=O)CSc2ccc(OC)cc2)[C@]2(C)C(C)CCC3(CCC(=O)C32)[C@@H](C)[C@@H]1O]

$^1$H-NMR (400 MHz, DMSO-$d_6$, δ, ppm, characteristic signals): 0.54 (d, 3H, J=7Hz, CH$_3$-16); 0.79 (d, 3H, J=7Hz, CH$_3$-17); 0.99 (s, 3H, CH$_3$-18); 1.29 (s, 3H, CH$_3$-15); 2.34 (bs, 1H, H-4); 3.37 (t, 1H, J=6Hz, H-11); AB-system (U$_A$=3.67, U$_B$=3.59, J=15Hz, CH$_2$-22); 3.71 (s, 3H, CH$_3$-25); 4.96 (m, 2H, H-20); 5.47 (d, 1H, J=8Hz, H-14); 6.03 (m, 1H, H-19); 6.85 (m, 2H, H-24); 7.32 (m, 2H, H-23).

Example 12

(Comparison):
14-O-[(2-Methoxy-phenylsulfanyl)-acetyl]mutilin

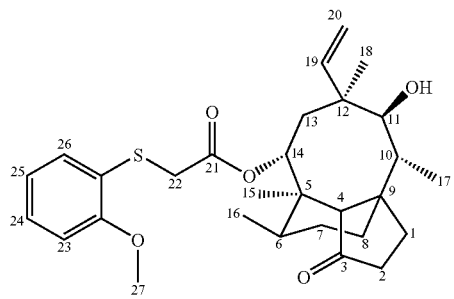 [SMILES: C=C[C@]1(C)C[C@@H](OC(=O)CSc2ccccc2OC)[C@]2(C)C(C)CCC3(CCC(=O)C32)[C@@H](C)[C@@H]1O]

$^1$H-NMR (400 MHz, DMSO-$d_6$, δ, ppm, characteristic signals): 0.55 (d, 3H, J=7Hz, CH$_3$-16); 0.79 (d, 3H, J=7Hz, CH$_3$-17); 0.98 (s, 3H, CH$_3$-18); 1.29 (s, 3H, CH$_3$-15); 2.34 (bs, 1H, H-4); 3.37 (t, 1H, J=6Hz, H-11); AB-system (U$_A$=3.74, U$_B$=3.64, J=15Hz, CH$_2$-22); 4.94 (m, 2H, H-20); 5.47 (d, 1H, J=8Hz, H-14); 6.03 (dd, 1H, J=11, and 18Hz, H-19); 6.86 (m, 1H, H-25); 6.96 (m, 1H, H-23); 7.14 (m, 1H, H-24); 7.21 (m, 1H, H-26).

Example 13

14-O-[(3,4-Dimethoxy-phenylsulfanyl)-acetyl]-mutilin

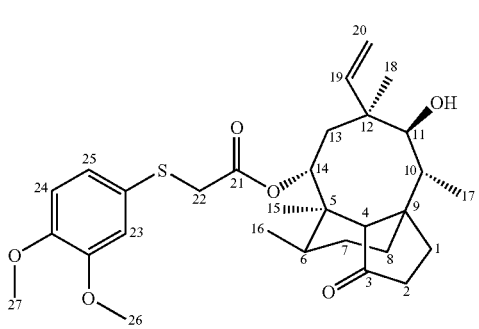 [SMILES: C=C[C@]1(C)C[C@@H](OC(=O)CSc2ccc(OC)c(OC)c2)[C@]2(C)C(C)CCC3(CCC(=O)C32)[C@@H](C)[C@@H]1O]

$^1$H-NMR (400 MHz, DMSO-$d_6$, δ, ppm, characteristic signals): 0.55 (d, 3H, J=7Hz, CH$_3$-16); 0.78 (d, 3H, J=7Hz, CH$_3$-17); 0.97 (s, 3H, CH$_3$-18); 1.29 (s, 3H, CH$_3$-15); 2.35 (bs, 1H, H-4); 3.37 (t, 1H, J=6 Hz, H-11); AB-system (U$_A$=3.74, U$_B$=3.64, J=15Hz, CH$_2$-22); 3.70 and 3.73 (2xs, 6H, CH$_3$-26 and 27); 4.94 (m, 2H, H-20); 5.47 (d, 1H, J=8Hz, H-14); 6.03 (m, 1H, H-19); 6.86 (d, 1H, J=8Hz, H-24); 6.92 (dd, 1H, J=2 and 8Hz, H-25); 7.00 (d, 1H, J=2Hz, H-23).

Example 14

(Comparison):
14-O-[(3-Methyl-phenylsulfanyl)-acetyl]-mutilin

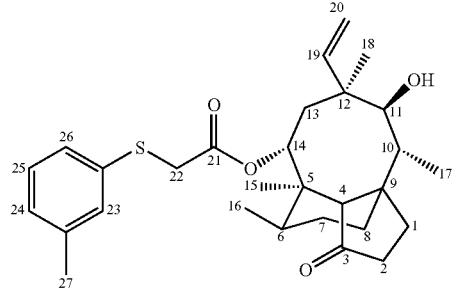

$^1$H-NMR (400 MHz, DMSO-$d_6$, δ, ppm, characteristic signals): 0.56 (d, 3H, J=7Hz, CH$_3$-16); 0.79 (d, 3H, J=7Hz, CH$_3$-17); 0.97 (s, 3H, CH$_3$-18); 1.30 (s, 3H, CH$_3$-15); 2.24 (s, 3H, CH$_3$-27); 2.35 (bs, 1H, H-4); 3.37 (t, 1H, J=6Hz, H-11); AB-system (U$_A$=3.80, U$_B$=3.73, J=16Hz, CH$_2$-22); 4.94 (m, 2H, H-20); 5.48 (d, 1H, J=8Hz, H-14); 6.03 (dd, 1H, J=11, and 18Hz, H-19); 6.98 and 7.23 (2xm, 4H, arom-H).

Example 15

14-O-[(3-Hydroxy-phenoxy)-acetyl]-mutilin

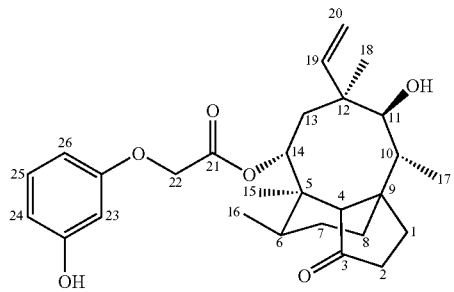 [SMILES: C=C[C@]1(C)C[C@@H](OC(=O)COc2cccc(O)c2)[C@]2(C)C(C)CCC3(CCC(=O)C32)[C@@H](C)[C@@H]1O]

To 196 mg (4 mmol) of sodium hydride in 20 mL of DMF 440 mg (4 mmol) of Benzene-1,3-diol is added at room temperature. After stirring the reaction for 30 min a solution of 2.12 g (4 mmol) of Pleuromutilintosylate in 30 mL of DMF is added and the reaction stirred at ambient temperature overnight. The reaction mixture is poured onto water, extracted three times with ethyl acetate and the organic phase washed three times with water. The organic phase is dried with Na$_2$SO$_4$, evaporated to dryness under reduced pressure and the residue is chromatographed on silica gel using dichloromethane/methanol 100:1 as mobile phase.

$^1$H-NMR (400 MHz, DMSO-d$_6$, δ, ppm, characteristic signals): 0.62 (d, 3H, J=7Hz, CH$_3$-16); 0.81 (d, 3H, J=7Hz, CH$_3$-17); 1.04 (s, 3H, CH$_3$-18); 1.33 (s, 3H, CH$_3$-15); 2.39 (bs, 1H, H-4); 3.40 (t, 1H, J=6Hz, H-11); AB-system (U$_A$=4.62, U$_B$=4.55, J=17Hz, CH$_2$-22); 5.00 and 5.07 (2xdd, 2H, J$_1$=2 and 11 Hz, J$_2$=2 and 18 Hz, H-20); 5.59 (d, 1H, J=8Hz, H-14); 6.10 (dd, 1H, J=11 and 18Hz, H-19); 6.27 (d, 1H, J=2 Hz, H-23); 6.28 and 6.35 (2xm, 2H, H-24 and 26); 7.00 (t, 1H, J=8Hz, H-25).

The following compounds are prepared in a similar fashion:

Example 16

14-O-[(4-Hydroxy-phenoxy)-acetyl]-mutilin

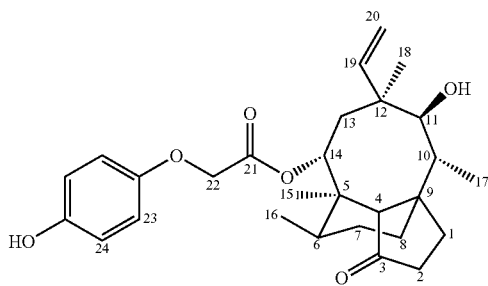 [SMILES: C=C[C@]1(C)C[C@@H](OC(=O)COc2ccc(O)cc2)[C@]2(C)C(C)CCC3(CCC(=O)C32)[C@@H](C)[C@@H]1O]

$^1$H-NMR (400 MHz, DMSO-d$_6$, δ, ppm, characteristic signals): 0.61 (d, 3H, J=7Hz, CH$_3$-16); 0.81 (d, 3H, J=7Hz, CH$_3$-17); 1.04 (s, 3H, CH$_3$-18); 1.33 (s, 3H, CH$_3$-15); 2.39 (bs, 1'-1, H-4); 3.40 (bs, 1H, H-11); AB-system (U$_A$=4.64, U$_B$=4.56, J=17Hz, CH$_2$-22); 5.01 and 5.06 (2xdd, 2H, J$_1$=2 and 11Hz, J$_2$=2 and 18Hz, H-20); 5.59 (d, 1H, J=8 Hz, H-14); 6.11 (dd, 1H, J=11 and 18Hz, H-19); 6.79 (s, 4H, H-23, 24).

Example 17

(Comparison): 14-O-[(2-Hydroxy-phenoxy)-acetyl]-mutilin

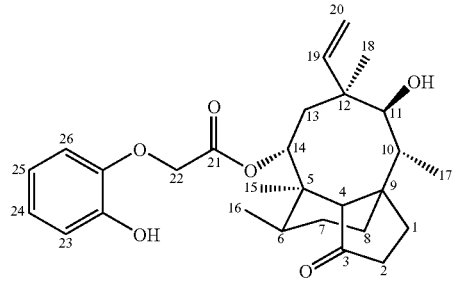 [SMILES: C=C[C@]1(C)C[C@@H](OC(=O)COc2ccccc2O)[C@]2(C)C(C)CCC3(CCC(=O)C32)[C@@H](C)[C@@H]1O]

$^1$H-NMR (400 MHz, DMSO-d$_6$, δ, ppm, characteristic signals): 0.62 (d, 3H, J=7Hz, CH$_3$-16); 0.80 (d, 3H, J=7Hz, CH$_3$-17); 1.04 (s, 3H, CH$_3$-18); 1.32 (s, 3H, CH$_3$-15); 2.39 (bs, 1H, H-4); 3.40 (bs, 1H, H-11); AB-system (U$_A$=4.68, U$_B$=4.60, J=17Hz, CH$_2$-22); 5.02 and 5.05 (2xdd, 2H, J$_1$=2 and 11Hz, J$_2$=2 and 18Hz, H-20); 5.60 (d, 1H, J=8Hz, H-14); 6.10 (dd, 1H, J=11 and 18Hz, H-19); 6.63 and 6.76 (2xm, 4H, H-23, 24, 25 and 26).

Example 18

14-O-[(3,5-Dihydroxy-phenoxy)-acetyl]-mutilin

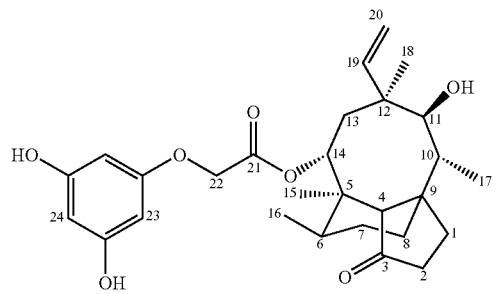 [SMILES: C=C[C@]1(C)C[C@@H](OC(=O)COc2cc(O)cc(O)c2)[C@]2(C)C(C)CCC3(CCC(=O)C32)[C@@H](C)[C@@H]1O]

$^1$H-NMR (400 MHz, DMSO-d$_6$, δ, ppm, characteristic signals): 0.62 (d, 3H, J=7Hz, CH$_3$-16); 0.81 (d, 3H, J=7Hz, CH$_3$-17); 1.04 (s, 3H, CH$_3$-18); 1.34 (s, 3H, CH$_3$-15); 2.39 (bs, 1H, H-4); 3.41 (t, 1H, J=6Hz, H-11); AB-system (U$_A$=4.53, U$_B$=4.45, J=16Hz, CH$_2$-22); 5.01 and 5.07 (2xdd, 2H, J$_1$=2 and 11Hz, J$_2$=2 and 18 Hz, H-20); 5.57 (d, 1H, J=8Hz, H-14); 5.72 (d, 2H, J=2Hz, H-23); 5.83 (t, 1H, J=2Hz, H-24); 6.10 (dd, 1H, J=11 and 18Hz, H-19).

Example 19

(Comparison):
14-O-[(3-Methyl-phenoxy)-acetyl]-mutilin

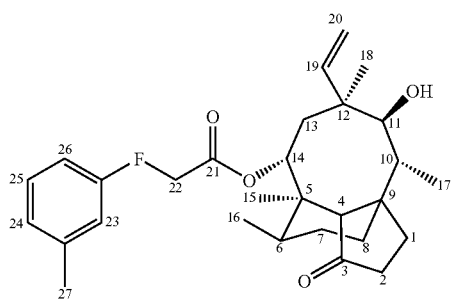

$^1$H-NMR (400 MHz, DMSO-$d_6$, δ, ppm, characteristic signals): 0.64 (d, 3H, J=7Hz, CH$_3$-16); 0.81 (d, 3H, J=7Hz, CH$_3$-17); 1.04 (s, 3H, CH$_3$-18); 1.33 (s, 3H, CH$_3$-15); 2.23 (s, 3H, CH$_3$-27); 2.40 (bs, 1H, H-4); 3.41 (bs, 1H, H-11); AB-system (U$_A$=4.68, U$_B$=4.62, J=17Hz, CH$_2$-22); 5.01 and 5.06 (2xd, 2H, J=11Hz and 18Hz, H-20); 5.60 (d, 1H, J=8Hz, H-14); 6.11 (dd, 1H, J=11, and 18Hz, H-19); 6.67 and 6.77 (2xd, 2H, J=7Hz, H-24 and 26); 6.68 (s, 1H, H-23); 7.12 (t, 1H, J=8Hz, H-25).

Antimicrobial Activity of Novel Pleuromutilin-derivatives with Aromatic Side-chain The antibacterial activity expressed as minimal inhibitory concentration (MIC) was determined according to the approved standard reference recommendations of CLSI (former NCCLS).

Examples 1, 7, 10, 15 and the other claimed compounds exhibited very good activity against the clinical relevant bacterial pathogens *Staphylococcus aureus, Enterococcus faecalis, Streptococcus pneumoniae, Moraxella catarrhalis* and *Escherichia coli* (see Tables 1 to 3). This in vitro activity was significantly better than that of the comparator compounds of examples 3, 6, 9, 12, 14 and 17 as the MICs of example 1 were by at least a factor of 2 lower against at least one of the strains shown in Table 1 than the MICs of the comparator compounds (see Tables 1 to 3).

TABLE 1

Antimicrobial activity of example 1 and the comparator compounds examples 3, 6 and 14 against selected bacterial pathogens shown as minimal inhibitory concentration (MIC, [μg/ml])

| Species | ATCC number | Strain | Example 1 (3-SMe, F) | Example 3 (2-SMe, F) | Example 6 (SMe, 2F) | Example 14 (3-SMe, CH$_3$) |
|---|---|---|---|---|---|---|
| *Staphylococcus aureus* (MSSA) | ATCC10390 | B6 | ≤0.0125 | 0.05 | 0.1 | 0.025 |
| *Staphylococcus aureus* (MSSA) | ATCC29213 | B7 | ≤0.0125 | 0.05 | 0.1 | 0.05 |
| *Enterococcus faecalis* | ATCC29212 | B4 | 3.2 | >25.6 | >25.6 | >6.4 |
| *Enterococcus faecalis* | ATCC51299 | B5 | >25.6 | >25.6 | >25.6 | >6.4 |
| *Moraxella catarrhalis* | ATCC43618 | B407 | ≤0.0125 | 0.025 | 0.05 | 0.0125 |
| *Escherichia coli* | ATCC25922 | B1 | >25.6 | >25.6 | >25.6 | >6.4 |
| *Streptococcus pneumoniae* | ATCC49619 | B11 | 0.04 | 0.16 | 0.32 | 0.16 |

TABLE 2

Antimicrobial activity of examples 7 and 10 and the comparator compounds examples 9, 12 and 14 against selected bacterial pathogens shown as minimal inhibitory concentration (MIC, [μg/ml])

| Species | ATCC number | Strain | Example 7 (SMe, OH) | Example 10 (SMe, OCH$_3$) | Example 9 (SMe, OH) | Example 12 (SMe, OCH$_3$) | Example 14 (SMe, CH$_3$) |
|---|---|---|---|---|---|---|---|
| *Staphylococcus aureus* (MSSA) | ATCC10390 | B6 | ≤0.0125 | 0.025 | ≤0.0125 | 0.2 | 0.025 |
| *Staphylococcus aureus* (MSSA) | ATCC29213 | B7 | ≤0.0125 | 0.025 | ≤0.0125 | 0.2 | 0.05 |
| *Enterococcus faecalis* | ATCC29212 | B4 | >25.6 | >25.6 | >25.6 | >25.6 | >6.4 |
| *Enterococcus faecalis* | ATCC51299 | B5 | >25.6 | >25.6 | >25.6 | >25.6 | >6.4 |
| *Moraxella catarrhalis* | ATCC43618 | B407 | ≤0.0125 | ≤0.0125 | ≤0.0125 | 0.1 | 0.0125 |

TABLE 2-continued

Antimicrobial activity of examples 7 and 10 and the comparator compounds examples 9, 12 and 14 against selected bacterial pathogens shown as minimal inhibitory concentration (MIC, [µg/ml])

| | | | MIC [µg/ml] | | | | |
|---|---|---|---|---|---|---|---|
| Species | ATCC number | Strain | Example 7 (OH, S-Me meta) | Example 10 (OCH3, S-Me meta) | Example 9 (OH, S-Me ortho) | Example 12 (OCH3, S-Me ortho) | Example 14 (CH3, S-Me meta) |
| *Escherichia coli* | ATCC25922 | B1 | >25.6 | >25.6 | >25.6 | >25.6 | >6.4 |
| *Streptococcus pneumoniae* | ATCC49619 | B11 | 0.02 | 0.04 | 0.16 | 0.16 | 0.16 |

TABLE 3

Antimicrobial activity of example 15 and the comparator compounds examples 14, 17 and 19 against selected bacterial pathogens shown as minimal inhibitory concentration (MIC, [µg/ml]).

| | | | MIC [µg/ml] | | | |
|---|---|---|---|---|---|---|
| Species | ATCC number | Strain | Example 15 (OH, OMe meta) | Example 14 (CH3, S-Me meta) | Example 17 (OH, OMe ortho) | Example 19 (CH3, OMe meta) |
| *Staphylococcus aureus* (MSSA) | ATCC10390 | B6 | 0.025 | 0.025 | 0.05 | 0.05 |
| *Staphylococcus aureus* (MSSA) | ATCC29213 | B7 | 0.025 | 0.05 | 0.05 | 0.05 |
| *Enterococcus faecalis* | ATCC29212 | B4 | 12.8 | >6.4 | >6.4 | >6.4 |
| *Enterococcus faecalis* | ATCC51299 | B5 | 25.6 | >6.4 | >6.4 | >6.4 |
| *Moraxella catarrhalis* | ATCC43618 | B407 | ≤0.0125 | 0.0125 | 0.0125 | 0.0125 |
| *Escherichia coli* | ATCC25922 | B1 | >25.6 | >6.4 | >6.4 | >6.4 |
| *Streptococcus pneumoniae* | ATCC49619 | B11 | 0.04 | 0.16 | 0.16 | 0.64 |

The invention claimed is:

1. A compound of formula (I) comprising:

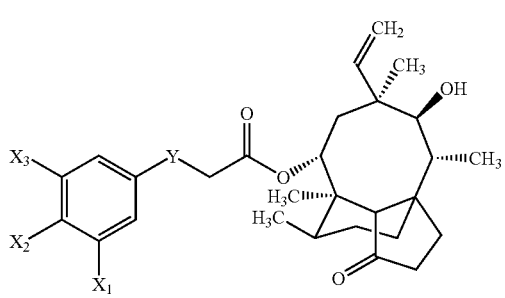

optionally in the form of a salt,
wherein
Y is oxygen or sulfur, and
$X_1$, $X_2$ and $X_3$ are independently of each other hydrogen, halogen, or ($C_{1-6}$)-alkoxy, with the proviso that at least one of $X_1$, $X_2$ and $X_3$ is other than hydrogen.

2. The compound of claim 1, which is selected from the group consisting of:

14-O-[(3-Fluoro-phenylsulfanyl)-acetyl]-mutilin,
14-O-[(4-Fluoro-phenylsulfanyl)-acetyl]-mutilin,
14-O-[(3,5-Difluoro-phenylsulfanyl)-acetyl]-mutilin,
14-O-[(3,4-Difluoro-phenylsulfanyl)-acetyl]-mutilin,
14-O-[(3-Methoxy-phenylsulfanyl)-acetyl]-mutilin,
14-O-[(4-Methoxy-phenylsulfanyl)-acetyl]-mutilin, and
14-O-[(3,4-Dimethoxy-phenylsulfanyl)-acetyl]-mutilin.

3. The compound of claim 1, in the form of a salt.

4. The compound of claim 1, wherein the compound is in a pharmaceutical composition.

5. A pharmaceutical composition comprising:
a compound of claim 1 in association with at least one pharmaceutical excipient.

6. The pharmaceutical composition of claim 5, further comprising another pharmaceutically active agent.

7. The compound of claim 2, in the form of a salt.

8. A pharmaceutical composition comprising:
a compound of claim 2 in association with at least one pharmaceutical excipient.

9. A pharmaceutical composition comprising:
a compound of claim 3 in association with at least one pharmaceutical excipient.

10. A compound of formula (I) comprising:

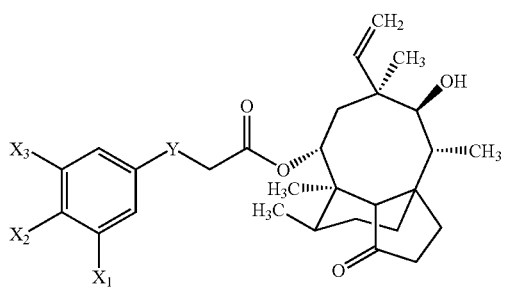

optionally in the form of a salt,
wherein
Y is oxygen or sulfur, and
$X_i$, $X_2$ and $X_3$ are independently of each other hydrogen or halogen, with the proviso that at least one of $X_1$, $X_2$ and $X_3$ is other than hydrogen.

11. The compound of claim 10, which is selected from the group consisting of:
14-O-[(3-Fluoro-phenylsulfanyl)-acetyl]-mutilin,
14-O-[(4-Fluoro-phenylsulfanyl)-acetyl]-mutilin,
14-O-[(3,5-Difluoro-phenylsulfanyl)-acetyl]-mutilin, and
14-O-[(3,4-Difluoro-phenylsulfanyl)-acetyl]-mutilin.

12. The compound of claim 10, in the form of a salt.

13. The compound of claim 11, in the form of a salt.

14. A pharmaceutical composition comprising:
a compound of claim 10 in association with at least one pharmaceutical excipient.

15. A pharmaceutical composition comprising:
a compound of claim 11 in association with at least one pharmaceutical excipient.

16. The compound of claim 2, which is selected from the group consisting of:
14-O-[(3-Methoxy-phenylsulfanyl)-acetyl]-mutilin,
14-O-[(4-Methoxy-phenylsulfanyl)-acetyl]-mutilin, and
14-O-[(3,4-Dimethoxy-phenylsulfanyl)-acetyl]-mutilin,
optionally in the form of a salt.

17. A method of treating bacterial infections caused by *Staphylococcus aureus, Enterococcus faecalis, Streptococcus pneumonia, Moraxelly catarrhalis* and *Escherichia coli*, comprising administering to a subject in need of such treatment an effective amount of a compound of claim 1, optionally in the form of a pharmaceutically acceptable salt.

18. A method of treating bacterial infections caused by *Staphylococcus aureus, Enterococcus faecalis, Streptococcus pneumonia, Moraxelly catarrhalis* and *Escherichia coli*, comprising administering to a subject in need of such treatment an effective amount of a compound of claim 2, optionally in the form of a pharmaceutically acceptable salt.

19. A method of treating bacterial infections caused by *Staphylococcus aureus, Enterococcus faecalis, Streptococcus pneumonia, Moraxelly catarrhalis* and *Escherichia coli*, comprising administering to a subject in need of such treatment an effective amount of a compound of claim 10, optionally in the form of a pharmaceutically acceptable salt.

20. A method of manufacturing a composition for treatment of diseases mediated by microbes, the method comprising:
obtaining a compound according to claim 1; and
including the compound in a medicament for the treatment of diseases mediated by microbes.

* * * * *